US007598065B2

(12) United States Patent
Kang et al.

(10) Patent No.: US 7,598,065 B2
(45) Date of Patent: Oct. 6, 2009

(54) **S-ADENOSYLMETHIONINE-6-N-LYSINE-METHYLTRANSFERASE FROM *NEUROSPORA CRASSA*, A GENE ENCODING THE SAME, A VECTOR AND HOST CELL CONTAINING THE SAME, AND METHOD FOR PRODUCING TRIMETHYLLYSINE USING THE HOST CELL**

(75) Inventors: Whan-Koo Kang, Daejeon (KR); Bheong-Uk Lee, Busan (KR); Young-Hoon Park, Seongnam (KR); Eun-Sung Koh, Suwon (KR); Jae-Yeong Ju, Seongnam (KR); Jin-Ho Lee, Yongin (KR); Hye-Won Kim, Seongnam (KR); Hye-Jin Choi, Seoul (KR)

(73) Assignee: CJ CheilJedang Corp. (KR)

( * ) Notice: Subject to any disclaimer, the term of this patent is extended or adjusted under 35 U.S.C. 154(b) by 2 days.

(21) Appl. No.: 11/994,938

(22) PCT Filed: Jul. 7, 2006

(86) PCT No.: PCT/KR2006/002660

§ 371 (c)(1),
(2), (4) Date: Jan. 7, 2008

(87) PCT Pub. No.: WO2007/007986

PCT Pub. Date: Jan. 18, 2007

(65) Prior Publication Data

US 2008/0199920 A1   Aug. 21, 2008

(30) Foreign Application Priority Data

Jul. 7, 2005   (KR) .................... 10-2005-0061143

(51) Int. Cl.
*C12N 9/10* (2006.01)
*C12N 9/00* (2006.01)
*C12N 1/20* (2006.01)
*C12N 15/00* (2006.01)
*C07H 21/04* (2006.01)

(52) U.S. Cl. .................. 435/193; 435/183; 435/252.3; 435/320.1; 536/23.2

(58) Field of Classification Search .............. None
See application file for complete search history.

(56) References Cited

U.S. PATENT DOCUMENTS 5,643,758 A * 7/1997 Guan et al. ............... 435/69.7

OTHER PUBLICATIONS

Borum et al. J Biol Chem. Aug. 25, 1977;252(16):5651-5.*
Sambrook et al. Moleecular cloning A Laboratory Manual, 2nd edition, Cold Spring Harbor, N.Y. 1989, pp. 8.46-8.52 and pp. 11.2-11.19.*
International Search Report for corresponding International Application No. PCT/KR2006/002660 dated Sep. 28, 2006.
Written Opinion of the International Searching Authority for corresponding International Application No. PCT/KR2006/002660 dated Sep. 28, 2006.
Peggy R. Borum, et al. "Purification of S-Adenosylmethionine: -N-L-Lysine Methyltransferase", J. Biol. Chem. vol. 252(16): pp. 5651-5655 (Aug. 25, 1977) (cited in the International Search Report mailed Sep. 28, 2006, filed in the Information Disclosure Statement filed Jan. 7, 2008).
Charles J. Rebouche, et al., "Carnitine Biosynthesis in *Neurospora crassa*: Enzymatic Conversion of Lysine to -N-Trimethyllysine", J. Baeteriol. vol. 126(3): pp. 1207-1214 (Jun. 1976)(cited in the International Search Report mailed Sep. 28, 2006, filed in the Information Disclosure Statement filed Jan. 7, 2008).
Samuel Nochumson, et al., "Cytochrome c-Specific Protein Methylase III from *Neurospora crassa*", Biochem., J. vol. 165(1): pp. 11-18 (Jul. 1, 1977)(cited in the International Search Report mailed Sep. 28, 2006, filed in the Information Disclosure Statement filed Jan. 7, 2008).
Egon Durban, et al., "Cytochrome c-specific Protein-Lysine Methyltransferase from *Neurospora crassa*", J. Biol. Chem. vol. 253(5): pp. 1247-1435 (Mar. 10, 1978)(cited in the International Search Report mailed Sep. 28, 2006, filed in the Information Disclosure Statement filed Jan. 7, 2008).
Extended European Search Report; Dated Apr. 28, 2009; European Patent Application No. 06769202.0.
Hans Peter Sorensen, et al.; "Advanced genetic strategies for recombinant protein expression"; Journal Of Biotechnology, Elsevier Science Publishers, Amsterdam, NL, vol. 115, No. 2, Jan. 26, 2005, pp. 113-128.
Castellar M R et al.,; "L(-)-carnitine production using a recombinant *Escherichia coli* strain", Enzyme and Microbial Technology, vol. 28, No. 9-10, Jun. 7, 2001, pp. 785-791.
Yoshida Mitsuru et al., "Expression of Neurospora crassa beta-tubulin, target protein of benzimidazole fungicides, in *Escherichia coli*", Pesticide Science, vol. 55, No. 3, Mar. 1999 (Mar. 1999), pp. 362-364.

* cited by examiner

*Primary Examiner*—Christian L Fronda
(74) *Attorney, Agent, or Firm*—Cantor Colburn LLP

(57) ABSTRACT

Provided is S-adenosylmethionine-6-N-lysine-methyl-transferase obtained from *Neurospora crassa*, a polynucleotide encoding the same, a vector and host cell containing the polynucleotide, and a method of producing trimethyllysine by culturing the host cell.

9 Claims, 4 Drawing Sheets ously. According to the method of the present invention, the host cell is cultured, and

SEQUENCE LISTING

```
<160> NUMBER OF SEQ ID NOS: 4

<210> SEQ ID NO 1
<211> LENGTH: 651
<212> TYPE: DNA
<213> ORGANISM: Neurospora crassa

<400> SEQUENCE: 1
atggccttcg gaaagcttta cacctacgag gcgaaccccc gctccacggc catcttggct    60
gtcgcgaagg ccaacaacct cgacctcgag gttatcaagg tcgaccttga ggctgccatc   120
gaggagtaca agaaggtcaa ccctctcggc aaggtcccca ccttcgttgg tgccgacggc   180
tacactctct tcgagtgcat cgccatcgcc atctatgtcg cttcccagaa cgagaagacc   240
actctcctcg gcaagaccaa gcaggactat gcctccatcc tgaagtggct ctctttcttc   300
aacaccgagg tccttccccc tcttgctggc tggtaccgcc ctctccttgg caaggctccc   360
tacaacaaga aggctgttga ggacgctcag gctactgccc tcaaggccat ctctgtcgcc   420
gaggcccacc tcaagaacaa caccttcctc gttggcgagc gcatcaccct tgccgatctc   480
ttcgccactg gcatcattgc ccgcggcttc gagttcttct tcgacaaggc ctggcgcgag   540
cagtacccca acgtcacccg ttggtacacc actgtctaca accagcccat ctactcggcc   600
gttgctcctc ccttcgctct ccttgatacc cccaagttga ccaacgtcta a             651

<210> SEQ ID NO 2
<211> LENGTH: 216
<212> TYPE: PRT
<213> ORGANISM: Neurospora crassa

<400> SEQUENCE: 2

Met Ala Phe Gly Lys Leu Tyr Thr Tyr Glu Ala Asn Pro Arg Ser Thr
1               5                   10                  15

Ala Ile Leu Ala Val Ala Lys Ala Asn Asn Leu Asp Leu Glu Val Ile
            20                  25                  30

Lys Val Asp Leu Glu Ala Ala Ile Glu Glu Tyr Lys Lys Val Asn Pro
        35                  40                  45
```

-continued

```
Leu Gly Lys Val Pro Thr Phe Val Gly Ala Asp Gly Tyr Thr Leu Phe
 50              55                  60

Glu Cys Ile Ala Ile Ala Ile Tyr Val Ala Ser Gln Asn Glu Lys Thr
 65              70                  75                  80

Thr Leu Leu Gly Lys Thr Lys Gln Asp Tyr Ala Ser Ile Leu Lys Trp
 85              90                  95

Leu Ser Phe Phe Asn Thr Glu Val Leu Pro Pro Leu Ala Gly Trp Tyr
100             105                 110

Arg Pro Leu Leu Gly Lys Ala Pro Tyr Asn Lys Lys Ala Val Glu Asp
115             120                 125

Ala Gln Ala Thr Ala Leu Lys Ala Ile Ser Val Ala Glu Ala His Leu
130             135                 140

Lys Asn Asn Thr Phe Pro Val Gly Glu Arg Ile Thr Leu Ala Asp Leu
145             150                 155                 160

Phe Ala Thr Gly Ile Ile Ala Arg Gly Phe Glu Phe Phe Asp Lys
165             170                 175

Ala Trp Arg Glu Gln Tyr Pro Asn Val Thr Arg Trp Tyr Thr Thr Val
180             185                 190

Tyr Asn Gln Pro Ile Tyr Ser Ala Val Ala Pro Pro Phe Ala Leu Leu
195             200                 205

Asp Thr Pro Lys Leu Thr Asn Val
210             215

<210> SEQ ID NO 3
<211> LENGTH: 33
<212> TYPE: DNA
<213> ORGANISM: Artificial Sequence
<220> FEATURE:
<223> OTHER INFORMATION: primer

<400> SEQUENCE: 3
ggaattccat atggccttcg gaaagcttta cac                           33

<210> SEQ ID NO 4
<211> LENGTH: 30
<212> TYPE: DNA
<213> ORGANISM: Artificial Sequence
<220> FEATURE:
<223> OTHER INFORMATION: primer

<400> SEQUENCE: 4
cgggatcctt agacgttggt caacttgggg                               30
```

S-ADENOSYLMETHIONINE-6-N-LYSINE-METHYLTRANSFERASE FROM *NEUROSPORA CRASSA*, A GENE ENCODING THE SAME, A VECTOR AND HOST CELL CONTAINING THE SAME, AND METHOD FOR PRODUCING TRIMETHYLLYSINE USING THE HOST CELL

BACKGROUND ART

The present invention relates to S-adenosylmethionine-6-N-lysine-methyltransferase (LMT) obtained from *Neurospora crassa*, a polynucleotide encoding the same, a vector and host cell containing the polynucleotide, and a method of producing trimethyllysine by culturing the host cell.

L-carnitine (3-hydroxy-4-trimethylaminobutyrate) generally exists in organisms and is a zwitterionic compound that carries long-chain activated fatty acids into the mitochondrial matrix across the inner mitochondrial membranes in the mitochondria. It is known that L-carnitine in the human body can be synthesized from lysine or protein lysine. Generally, in a mammal, protein lysine is used as a precursor of L-carnitine biosynthesis, but free lysine is used in *Neurospora crassa*. In L-carnitine biosynthesis, ε-N,N,N-trimethyllysine, ε-N,N,N-trimethyl-β-hydroxyllysine, a N,N,N-trimethylamino butyraldehyde intermediate, and γ-butyrobetaine are produced, and it is supposed that γ-butyrobetaine is hydroxylated by γ-butyrobetaine hydroxylase to become L-carnitine.

Even in the prior art, when L-carnitine is biosynthesized from free lysine in *Neurospora crassa*, an enzyme participating in the first step reaction of converting ε-N,N,N-trimethyllysine to L-lysine is not known. The enzyme can be usefully employed in producing L-carnitine from free lysine.

The inventors of the present invention have tried to produce a microorganism that uses an inexpensive precursor and also has a high production efficiency of L-carnitine, and found a protein and gene having activity of converting L-lysine from *Neurospora crassa* to 6-N-trimethyllysine, thus completing the present invention.

DETAILED DESCRIPTION OF THE INVENTION

Technical Problem

Figure 1:
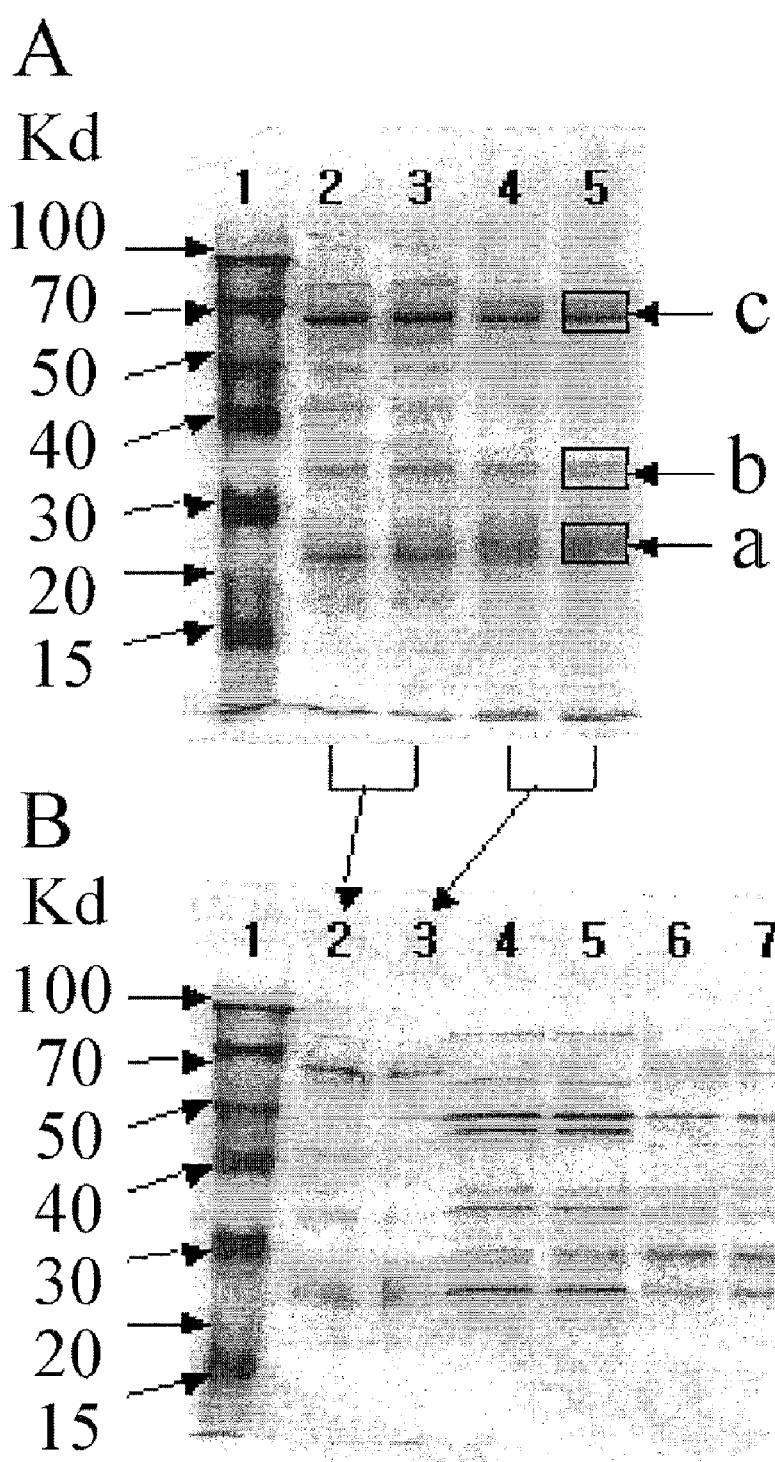
FIG. 1 is a diagram showing results of a natural-PAGE or SDS-PAGE analysis of an eluted solution obtained by lysing *Neurospora crassa* culture and performing DEAE column chromatography for the lysate.

The present invention provides a protein having an activity of converting L-lysine from *Neurospora crassa* to 6-N-trimethyllysine and a gene encoding the same.

The present invention also provides a vector and host cell containing the gene.

The present invention also provides a method of producing trimethyllysine by culturing the host cell.

Technical Solution

According to an aspect of the present invention, there is provided a protein that has an amino acid sequence of SEQ ID NO: 2 and activity of S-adenosylmethionine-6-N-lysine-methyltransferase.

The protein according to the present invention is derived from *Neurospora crassa*, has an amino acid sequence of SEQ ID NO: 2, and has activity of S-adenosylmethionine-6-N-lysine-methyltransferase. In the present invention, "S-adenosylmethionine-6-N-lysine-methyltransferase activity" is intended to mean an activity of catalyzing a reaction of forming trimethyllysine from L-lysine using L-lysine as a substrate.

According to another aspect of the present invention, there is provided a polynucleotide encoding an amino acid sequence of SEQ ID NO: 2. An example of the polynucleotide is a polynucleotide having a nucleotide sequence of SEQ ID NO: 1.

According to another aspect of the present invention, there is provided a vector containing the polynucleotide that encodes an amino acid sequence of SEQ ID NO: 2. In the present invention, "vector" denotes a nucleic acid construct that can serve as a vehicle capable of delivering the polynucleotide. The vector, for example, a vector derived from plasmid and a vector derived from viruses, includes a nucleic acid construct that can be not only duplicated, but also not duplicated in an organism. Therefore, the terms "plasmid", "vector" and "cassette" are interchangeably used in the present invention. In addition, the vector can include a regulatory sequence that regulates the expression of a gene, such as a promoter, an operator, an mRNA ribosome binding site and transcription/translation signals, and a sequence that makes it easier for a gene to be manipulated.

According to another aspect of the present invention, there is provided a host cell containing polynucleotide that encodes an amino acid sequence of SEQ ID NO: 2. The host cell may be a microorganism that belongs to *Escherichia* genus, and preferably *E. coli* BL21 (DE3) CJ2004-1 (Accession number KCCM-10637).

According to another aspect of the present invention, there is provided a method of producing trimethyllysine, the method comprising culturing a host cell containing polynucleotide encoding an amino acid sequence of SEQ ID NO: 2 in the presence of free lysine. In the present invention, the host cell may be BL21 (DE3) CJ2004-1 (Accession number KCCM-10637). The culture can be performed according to selected host cells under conditions of an appropriate medium and culture that are conventionally used. According to the method of the present invention, the host cell is cultured, and then S-adenosylmethionine-6-N-lysine-methyltransferase is produced in a cell or culture solution, and finally lysine is converted to trimethyllysine. The method according to the present invention can be used for finally producing L-carnitine by reacting the produced trimethyllysine with an enzyme in a cell or in vitro which is associated with biosynthesis of L-carnitine. The produced L-carnitine can be purified by a conventional method that is known to those skilled in the art.

ADVANTAGEOUS EFFECTS

S-adenosylmethionine-6-N-lysine-methyltransferase according to an embodiment of the present invention can convert free lysine to trimethyllysine in vitro and in vivo.

A gene according to an embodiment of the present invention can encode S-adenosylmethionine-6-N-lysine-methyltransferase, a vector and host cell according to an embodiment of the present invention express S-adenosylmethionine-6-N-lysine-methyltransferase, thereby being usefully used in a method of converting free lysine to trimethyllysine.

According to the method of the present invention, trimethyllysine can be produced from free lysine.

BEST MODE

Hereinafter, the present invention will be described in further detail with reference to the following examples. These examples are for illustrative purposes only and are not intended to limit the scope of the present invention.

EXAMPLE

Example 1

Protein Separation of S-adenocylmethionine-6-N-lysine-methyltransferase from *Neurospora crassa* and Confirmation of the Function Thereof

*Neurospora crassa* was cultured and a cell was collected. Then, the cell was lysed using 2 mM of DTT and 1M of pH 7.4 potassium phosphate buffer including 0.2 mM of EDTA, and then a protein was extracted. The protein was precipitated by slowly adding ammonium sulfate into the obtained supernatant to reach a final saturation concentration of 50%, and then a small amount of 0.1 M of pH 7.4 potassium phosphate buffer was added to the precipitated protein after centrifugal separation. The solution was desalted using a T1 dialysis membrane. The desalted sample was purified using a DEAE column. At this time, washing was performed by using 0.1 M of pH 7.4 potassium phosphate buffer as a washing buffer, and elution was performed by using 0.1 M of pH 7.4 potassium phosphate buffer including 0.3 M of NaCl as an eluting buffer and pooled the eluted solution. Thereafter, the resulted sample was desalted using a T1 dialysis membrane. The desalted sample was purified using a CM column. 0.1 M of pH 7.4 potassium phosphate buffer was used as a washing buffer of the column, and a sample that was not adsorbed onto the column and flowed out of the column was all pooled.

The protein sample was loaded on the DEAE column again, and then concentration gradient elution was performed to reach a NaCl concentration of 0-0.3 M using 0.1 M of pH 7.4 potassium phosphate buffer. A protein analysis was performed for the sample purified using natural-PAGE and SDS-PAGE.

FIG. 1 is a diagram showing results of a natural-PAGE or SDS-PAGE analysis of a eluted solution obtained after the purification process described above was performed and after DEAE column chromatography was performed. In FIG. 1A, lane 1 represents a marker, lane 2 and 3 represent results of a natural-PAGE analysis of DEAE elution peak 2, and lane 4 and 5 represent results of a natural-PAGE analysis of DEAE elution peak 3. In FIG. 1B, lane 1 represents a marker, lane 2 represents a result of a natural-PAGE analysis of DEAE elution peak 2, lane 3 represents a result of a natural-PAGE analysis of DEAE elution peak 3, lane 4 and 5 represent results of a SDS-PAGE analysis of DEAE elution peak 2, and lane 6 and 7 represent results of a SDS-PAGE analysis of DEAE elution peak 3.

From the results of FIG. 1, bands a, b and c were chosen as an LMT candidate protein, and the activity of each protein was measured. First, a gel corresponding to each band was cut out, and then the gel was crushed by a homogenizer. Then, 5 ml of 1 g/L lysine (final concentration 500 mg/L) and 2 ml of 1 g/L methyl donor, S-adenosylmethionine were added to the resulted product and slowly stirred at 28° C. for 24 hours to analyze a trimethyllysine peak using HPLC.

Figure 2:
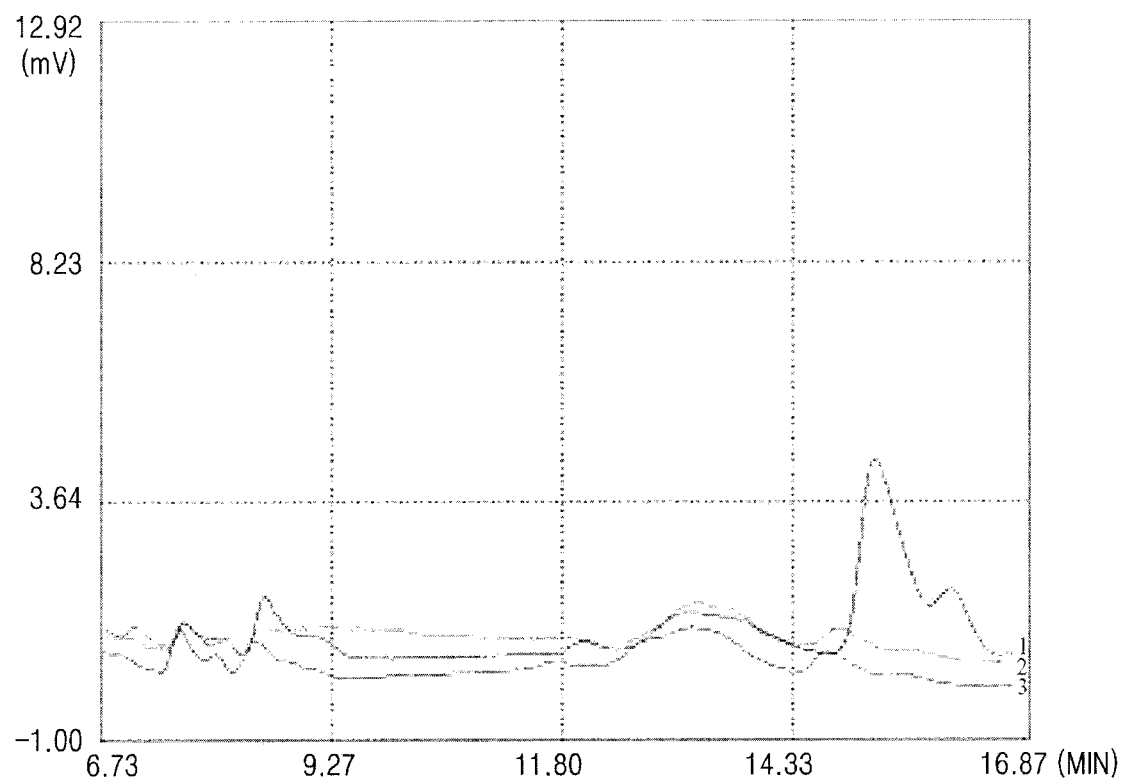
FIG. 2 is a graph showing results of measuring trimethyllysine through HPLC after protein bands a, b and c are reacted with lysine and S-adenosylmethionine.
Figure 3:
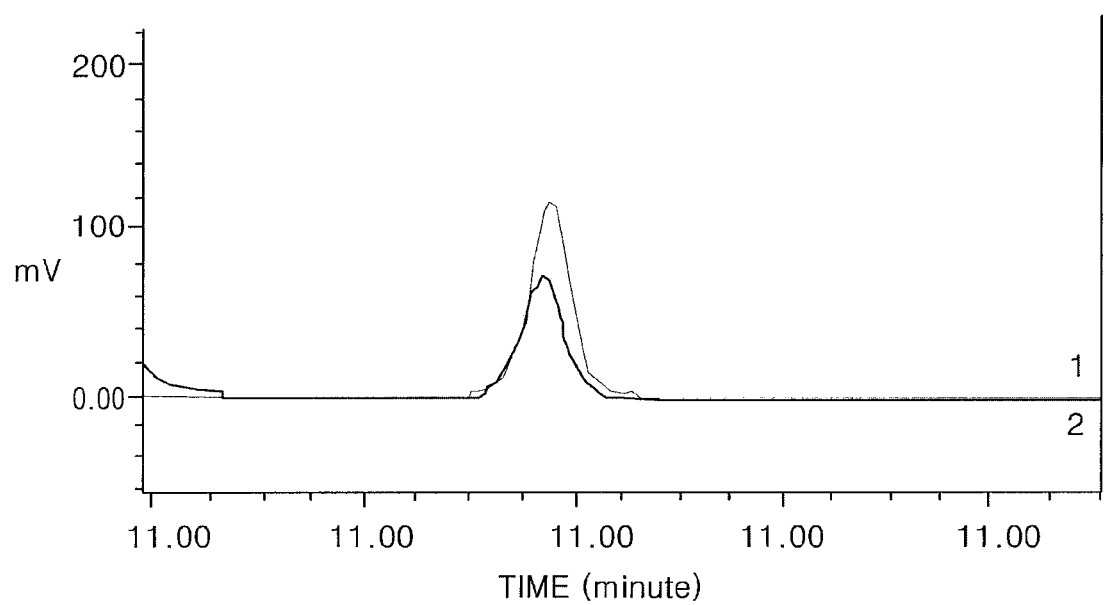
FIG. 3 is a graph showing results of analyzing a sample obtained by reacting the band a protein with lysine band of a and trimethyllysine standard through HPLC.

FIG. 2 is a graph showing results of measuring trimethyllysine through HPLC after protein bands a, b and c are reacted with lysine and S-adenosylmethionine. As illustrated in FIG. 2, in a sample reacted with the band a, a peak considered as trimethyllysine was confirmed around a retention time of 15 minutes. In FIG. 2, 1, 2 and 3 represent results corresponding to each band a, b and c. To more exactly confirm the bands, a sample obtained by reacting with the band a with a lysine was compared with a trimethyllysine standard.

FIG. 3 is a graph showing results of analyzing a sample obtained by reacting the protein band a with lysine and comparing it with a trimethyllysine standard through HPLC. As illustrated in FIG. 3, a peak time, a time at which a voltage has the highest value, of the band a is exactly consistent with the trimethyllysine standard. Therefore, it is confirmed that the band a includes S-adonosylmethionine-6-N-lysine-methyltransferase, LMT. In FIG. 3, 1 and 2 refers to results corresponding to each standard and the band a. Separate HPLC graphs are integrated in FIGS. 2 and 3.

Next, an N-terminal sequence was analyzed to obtain an amino acid sequence of LMT protein. First, a protein in SDS-PAGE gel was transferred to a PVDF membrane, and then protein bands were cut out to analyze the N-terminal sequence by Edman method. In particular, phenylisothiocyanate (PTC) was reacted with peptide at pH 8-9 and room temperature, and thus PTC-peptide in which an N-terminal was thiocarbamylated was obtained, thereafter, the PTC-peptide was reacted under acidic condition to separate only an N-terminal amino acid therefrom. The separated amino acid was extracted with ethylacetate, identified with HPLC, and analyzed. As a result, it was confirmed that the N-terminal sequence was AFGKL (SEQ ID NO: 5). a search for entire genome sequence of known *Neurospora crassa* was conducted based on the confirmed N-terminal amino acid sequence. As a result, a protein and gene having amino acid sequence that is consistent with the N-terminal sequence of the LMT, and nucleotide sequence were confirmed.

Example 2

Confirmation of a Gene Encoding LMT from *Neurospora crassa*

In the present example, a cDNA library from *Neurospora crassa* was constructed, and a gene encoding LMT therefrom was confirmed.

(1) Construction of the cDNA Library from *Neurospora crassa*

Using mRNA separated from *Neurospora crassa* as a template, cDNA was produced through PCR that uses polyT as primer. The obtained cDNA was inserted into λAD5 cloning vector using EcoRI and XhoI. Next, in order to obtain cDNA pool in the form of plasmid, the following processes were performed: E. coli BNN322 was cultured overnight in LB Km+0.2% maltose; cells were collected using centrifugal separation; the cells were resuspended in a solution of 1 ml of 10 mM $MgSO_4$; the resuspended cells were incubated with $3.5 \times 10^7 \lambda$ containing cDNA pool at 30° C. for 30 minutes without stirring; 2 ml of LB culture medium was added thereto, and the infected bacteria was shake-cultured at 30° C. for more than one hour; the resulted product was plated on LB+ ampicillin (75 μl/ml) culture medium; and plasmids were separated from the produced colonies to form a cDNA library pool.

(2) Confirmation of a Gene (lmt) of S-adenosylmethionine-6-N-lysine-methyltransferase (LMT)

Using LMT protein and information on gene sequence thereof obtained in Example 1, a primer set comprising oligonucleotide of SEQ ID. Nos. 3 and 4 was constructed to amplify lmt gene.

Figure 4:
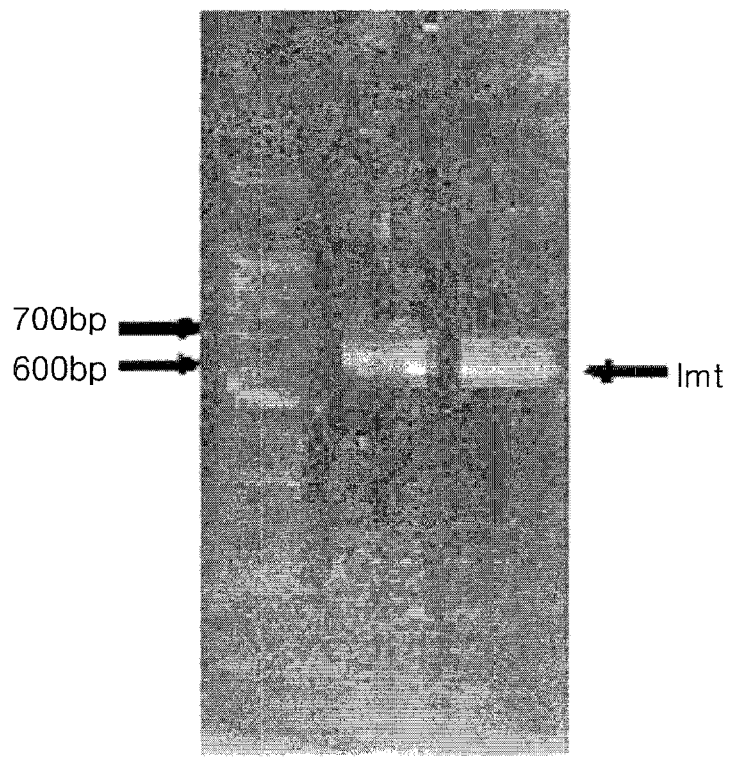
FIG. 4 is a diagram showing results of analyzing a PCR product of a gene of S-adenosylmethionine-6-N-lysine-methyltransferase using an agarose electrophoresis method.

Next, using the cDNA library as a template, a gene of S-adenosylmethionine-6-N-lysine-methyltransferase was amplified through PCR that used the primer set as a primer. The obtained PCR product was analyzed by agarose electrophoresis. As a result, a band was confirmed at about 0.65 kb, and a gene base sequence was confirmed by an automated base sequence analysis (SEQ ID NO: 1). As a result of a search for similar information to that on the analyzed base sequence using a search engine of NCBI BLAST, a gene having a 100% identity with the lmt gene was found in the Neurospora genome sequence, and it was confirmed that the gene was referred to as only hypothetical protein in terms of its function. In addition, an amino acid sequence of S-adenosylmethionine-6-N-lysine-methyltransferase is deduced from a sequence of the gene as a SEQ ID NO: 2. FIG. 4 is a diagram showing results of analyzing a PCR product of a gene of S-adenosylmethionine-6-N-lysine-methyltransferase by agarose electrophoresis.

Next, the PCR product was digested with NdeI and BamHI and ligated to pUC19 digested with the same enzymes, and then E. coli DH5α was transformed with the resulted product. Thereafter, the transformant was separated by a blue/white assay. As a result, it was confirmed that a plasmid onto which a gene S-adenosylmethionine-6-N-lysine-methyltransferase was inserted existed.

Example 3

Expression of a Gene of S-adenosylmethionine-6-N-lysine-methyltransferase in E. coli In the present example, an E. coli expression vector was constructed in order to express a gene of the S-adenosylmethionine-6-N-lysine-methyltransferase from Neurospora crassa in E. coli. Then, the vector was introduced into E. coli and whether the E. coli expressed the gene of the S-adenosylmethionine-6-N-lysine-methyltransferase from Neurospora crassa was determined.

(1) Construction of E. coli Expression Vector pT7-7LMT vector for expressing a gene of S-adenosylmethionine-6-N-lysine-methyltransferase in E. coli was constructed.

Figure 5:
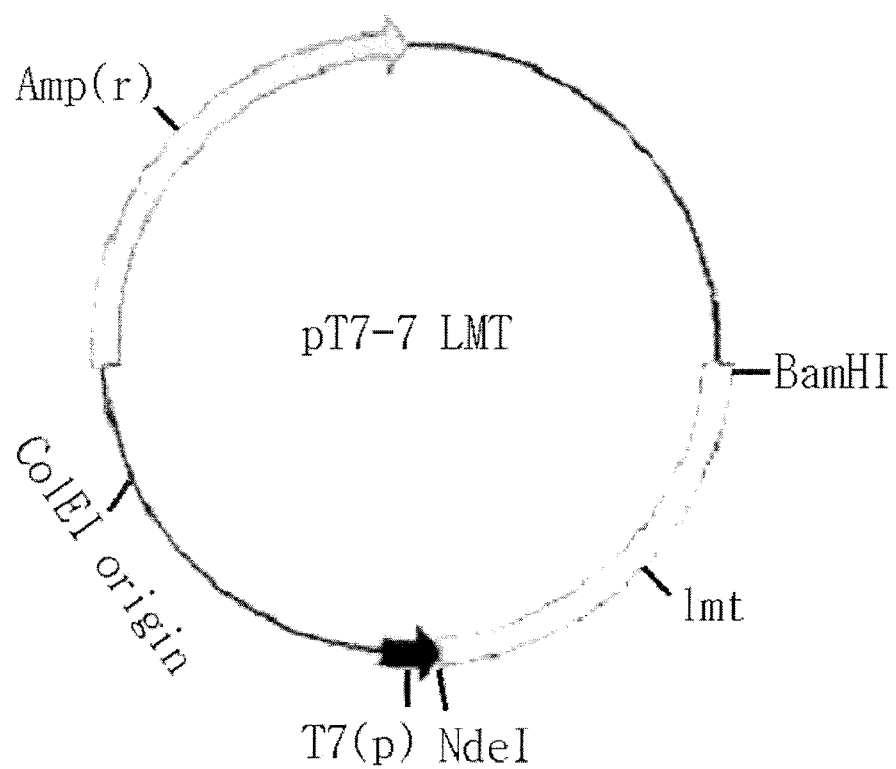
FIG. 5 is a diagram showing a constitution of pT7-7 LMT.

First, a gene of S-adenosylmethionine-6-N-lysine-methyltransferase from a plasmid including the same was digested with a restriction enzyme, such as NdeI and BamHI and then only DNA of the gene of S-adenosylmethionine-6-N-lysine-methyltransferase was separated and purified by doing electrophoresis in a low melting point agarose gel. Then, the DNA was inserted into pT7-7 treated with NdeI and BamHI (FIG. 5). FIG. 5 is a diagram representing a constitution of pT7-7 LMT. The ligation mixture was inserted into E. coli DH5α and the bacteria were transformed, and then the transformant was separated in a solid plating medium containing ampicillin. The recombinant plasmid was separated from the separated transformant and digested with NdeI and BamHI. As a result, insertion of the gene of S-adenosylmethionine-6-N-lysine-methyltransferase was confirmed and the vector was referred to as pT7-7LMT.

(2) Construction of E. coli BL21 (DE3) into which pT7-7LMT is Introduced

E. coli BL21 DE3 was transformed with pT7-7 LMT vector. 40 μl of E. coli BL21 DE3 and 1 μl of pT7-7-LMT vector were mixed, placed in cold cuvettes with 2 mm gap and transformed by electroporation under a condition of 2.5 kV, 200Ω, and 25 μF. The obtained transformant was plated on a solid plating medium containing ampicillin, and then a plasmid was purified from the transformant selected therefrom and digested with NdeI and BamHI. As a result, introduction of pT7-7LMT into the plasmid was confirmed by confirming the size of the inserted gene and the plasmid, and it was referred to as BL21 (DE3)/pT7-7LMT.

(3) Expression of S-adenosylmethionine-6-N-lysine-methyltransferase in E. coli

Figure 6:
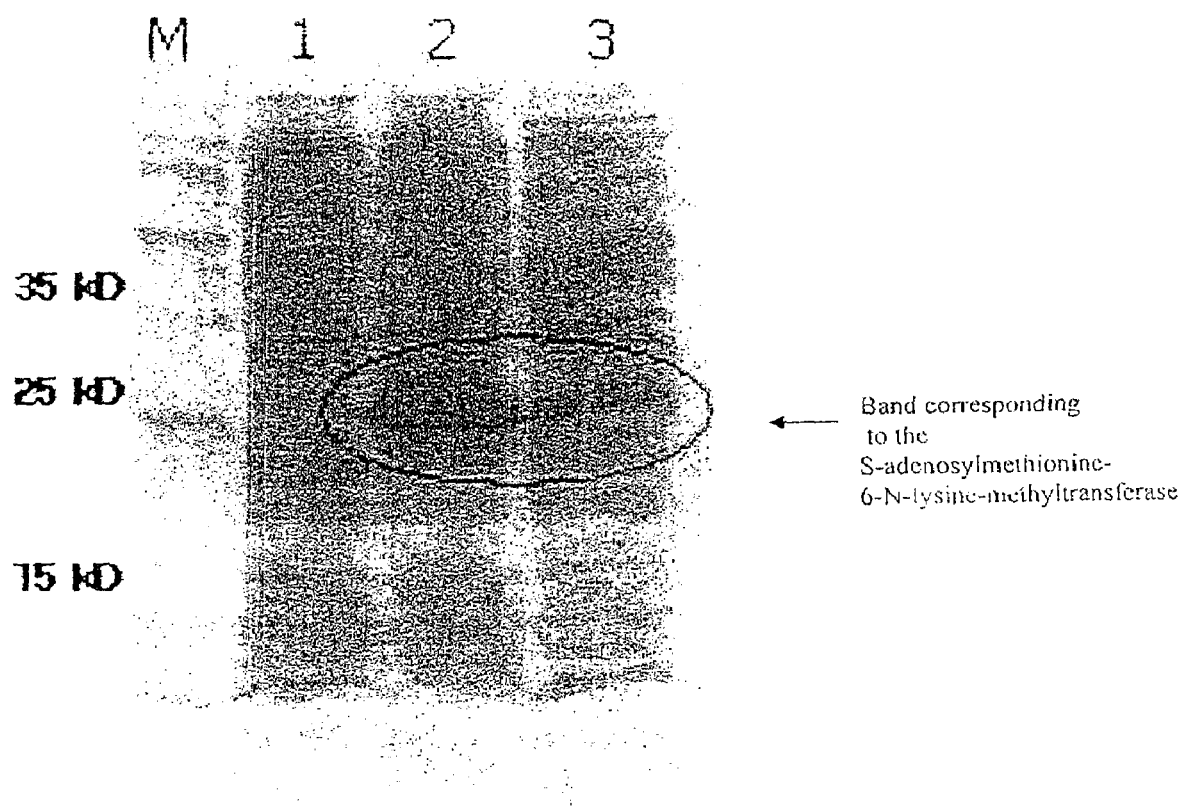
FIG. 6 is a diagram showing results of an SDS-PAGE analysis of supernatant obtained by culturing *E. coli* containing S-adenosylmethionine-6-N-lysine-methyltransferase gene obtained from *Neurospora crassa* in the presence of IPTG and lysing the fungal body obtained therefrom.

In order to confirm an expression of S-adenosylmethionine-6-N-lysine-methyltransferase, BL21 (DE3)/pT7-7LMT in which E. coli BL21 (DE3) was transformed with pT7-7LMT was cultured. BL21 (DE3)/pT7-7LMT was cultured to $OD_{600}$ 0.6 in 50 ml of LB medium or a 250 ml flask equipped with a baffle in which LB medium including ampicillin was placed therein, and then cultured for more than 4 hours after 1 mM of IPTG was added therein. Centrifugation was performed at 4,000×g for 15 minutes and cells were collected. Then, the cells were resuspended with 1 ml of a lysis solution (140 mM NaCl, 200 g/l glycerol and 1 mM DTT in 10 mM of pH 7.4 sodium phosphate buffer solution). The resulted cultured cells were covered with ice and then the cells were lysed 5 times for 10 seconds each using an ultrasonic homogenizer. After that, centrifugation was performed at 4° C., 10,000×g for 20-30 minutes, and then cell debris was removed and only supernatant was collected. About 25 kD of S-adenosylmethionine-6-N-lysine-methyltransferase was confirmed by SDS-PAGE (FIG. 6). FIG. 6 is a diagram showing results of SDS-PAGE analysis of a supernatant obtained by culturing E. coli containing S-adenosylmethionine-6-N-lysine-methyltransferase gene from Neurospora crassa in the presence of IPTG and lysing bacteria obtained therefrom.

In FIG. 6, lane M refers to a marker, lane 1 refers to negative control, and lane 2 and 3 refer to a cell lysate, and a circled part in lane 2 and 3 refers to a band of a position of 25 kD corresponding to LMT.

Example 4

Construction of Trimethyllysine Using E. coli BL21 (DE3)/pT7-7LMT

E. coli BL21 (DE3)/pT7-7LMT constructed in Example 2 was cultured to $OD_{600}$ 0.6 in 50 ml of LB medium or a 250 ml flask equipped with a baffle in which an LB medium including ampicillin was placed, and then cultured at 28° C. for more than 8 hours to form an exact tertiary structure of an enzyme and prevent an inclusion body from forming after 1 mM of IPTG was added therein. During culturing, 500 mg/L of L-lysine and 200 mg/L of S-adenosylmethionine were added as a reaction solution, and a trimethyllysine content of a culture solution was measured. The results are shown in Table 1.

Trimethyllysine was measured by HPLC under the following conditions. SUPELCOSIL LC-DABS from Supelco was used as a column, A buffer was made such that 0.1% of trifluoroacetic acid (TFA) was added to a buffer in which a distilled water and acetonitrile were mixed in a ratio of 8 to 2, and B buffer was made such that 0.1% of TFA was added to a buffer in which a distilled water and acetonitrile were mixed in a ratio of 2 to 8. Trimethyllysine was analyzed using a linear concentration gradient method, maintaining a flow velocity of 0.8 ml/min.

TABLE 1

| Tested Materials | Trimethyllysine (µg/ml) |
|---|---|
| E. coli BL21 (DE3)/pT7-7 (IPTG induction) + 500 mg/L lysine + 200 mg/L Ado-Met | 0.0 |
| E. coli BL21 (DE3)/pT7-7 LMT(IPTG induction) + 500 mg/L lysine + 200 mg/L Ado-Met | 20.0 |

As shown in Table 1, it was confirmed that a gene of S-adenosylmethionine-6-N-lysine-methyltransferase from *Neurospora crassa* was expressed in *E. coli*, and L-lysine was converted into trimethyllysine therefrom.

*E. coli* BL21 (DE3)/pT7-7LMT obtained in the present example was deposited on Dec. 13, 2004, in the Korean Culture Center of Microorganisms (KCCM), which is an International Depositary Authority under Budapest Treaty (deposited name: BL21 (DE3) CJ2004-1: Accession number KCCM-10637).

The invention claimed is:

1. An isolated protein having an activity of S-adenosylmethionine-6-N-lysine-methyltransferase having the amino acid sequence of SEQ ID NO: 2 that catalyzes a formation of 6-N-trimethyllysine from L-lysine.

2. An isolated polynucleotide encoding the amino acid sequence of SEQ ID NO: 2

3. The polynucleotide of claim 2, wherein the polynucleotide has the nucleotide sequence of SEQ ID NO: 1.

4. A vector containing the polynucleotide of claim 2.

5. An isolated host cell containing the polynucleotide of claim 2.

6. The host cell of claim 5, wherein the host cell is *E. coli* BL21 (DE3) CJ2004-1(Accession number KCCM-10637).

7. A method of producing trimethyllysine, the method comprising culturing the host cell according to claim 5 in the presence of lysine.

8. A vector containing the polynucleotide of claim 3.

9. A method of producing trimethyllysine, the method comprising culturing the host cell according to claim 6 in the presence of lysine.

* * * * *